(12) United States Patent
Hotier et al.

(10) Patent No.: US 6,969,495 B1
(45) Date of Patent: Nov. 29, 2005

(54) MAT ELEMENT THAT HAS A DISTRIBUTION FUNCTION

(75) Inventors: Gérard Hotier, Rueil Malmaison (FR); Pierre Renard, Saint Nom la Breteche (FR); Xavier Decoodt, Montreuil (FR)

(73) Assignee: Institut Francais du Petrole, Rueil-Malmaison (FR)

( * ) Notice: Subject to any disclaimer, the term of this patent is extended or adjusted under 35 U.S.C. 154(b) by 994 days.

(21) Appl. No.: 09/590,380

(22) Filed: Jun. 9, 2000

(30)  Foreign Application Priority Data

Jun. 9, 1999  (FR) .................................. 99 07307

(51) Int. Cl.$^7$ .............................. B01J 8/04; B01J 10/00
(52) U.S. Cl. ...................... 422/190; 422/195; 422/220; 422/180; 422/189; 422/188; 261/97; 261/98; 261/146; 261/147; 261/75; 261/114.5
(58) Field of Search ................. 422/190, 194, 422/195, 220, 180, 189, 188; 261/97, 98, 261/146, 147, 75, 114.5, 114.1; 202/225, 202/270

(56)  References Cited

U.S. PATENT DOCUMENTS

| | | | | |
|---|---|---|---|---|
| 2,369,478 A | * | 2/1945 | Mekler et al. ............... | 422/191 |
| 2,461,331 A | * | 2/1949 | Leesemann .................. | 585/628 |
| 3,592,612 A | | 7/1971 | Ballard et al. ................ | 23/288 |
| 3,705,016 A | * | 12/1972 | Ludwigesen et al. ........ | 422/191 |
| 3,787,189 A | * | 1/1974 | Muffat et al. ................ | 422/310 |
| 4,221,638 A | * | 9/1980 | Jones, Jr. ..................... | 202/121 |
| 4,836,989 A | * | 6/1989 | Aly et al. ..................... | 422/195 |
| 4,960,571 A | * | 10/1990 | Bhagat et al. ............... | 422/194 |
| 5,403,560 A | * | 4/1995 | Deshpande et al. .......... | 422/190 |
| 5,462,719 A | | 10/1995 | Pedersen et al. ............ | 422/195 |
| 5,989,502 A | * | 11/1999 | Nelson et al. ............... | 422/194 |

FOREIGN PATENT DOCUMENTS

| | | |
|---|---|---|
| EP | 0 074 815 | 3/1983 |
| EP | 0 472 335 | 2/1992 |

* cited by examiner

*Primary Examiner*—Glenn Caldarola
*Assistant Examiner*—Alexis Wachtel
(74) *Attorney, Agent, or Firm*—Millen, White, Zelano & Branigan P.C.

(57)  ABSTRACT

For use in a separation column, a mat element or a beam element has at least: an upper part 2; at least one distributor-collector part (3) having one or more secondary orifices (7i) and at least one main orifice (6), whereby the passage sections of orifices (8) and (7i) are different; and a lower part (4). The distributor-collector part or parts (3) arranged between the upper part (2) and the lower part (4). A sealing element (5a) arranged between the distributor-collector part (3) and the upper part (2), and a sealing element (5b) arranged between the distributor-collector part (3) and the lower part (4). A separation element (8) arranged at distributor-collector part (3), thus delimiting two spaces (3a, 3b) for circulation of fluids.

33 Claims, 7 Drawing Sheets

Figure 5:
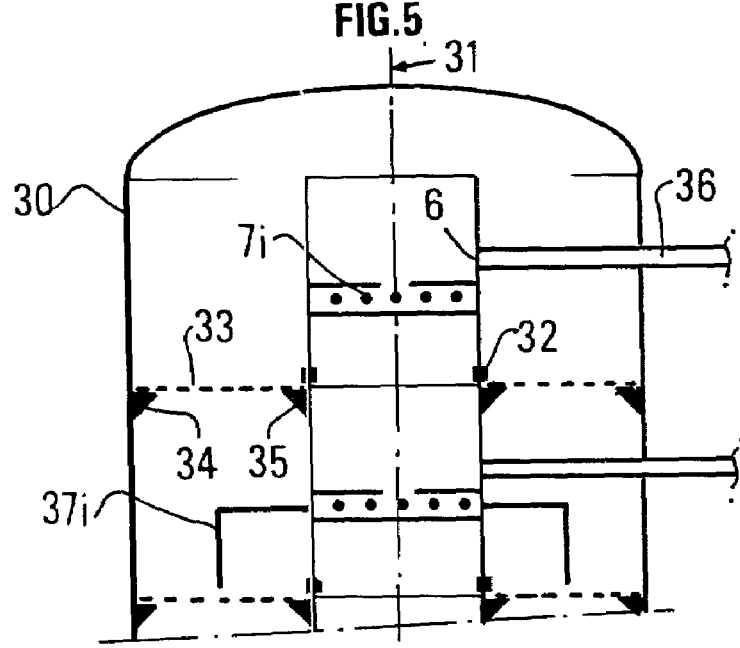

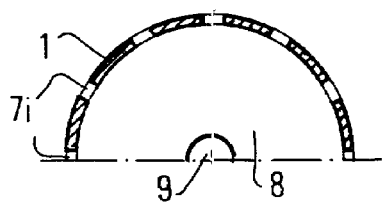
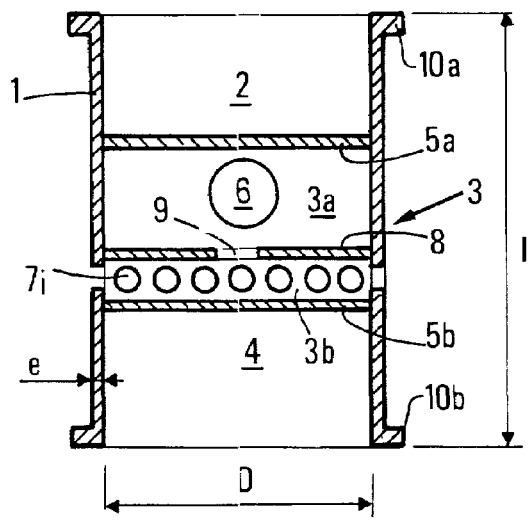
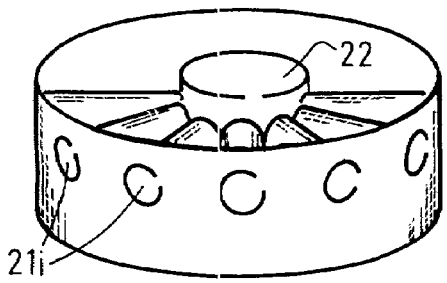
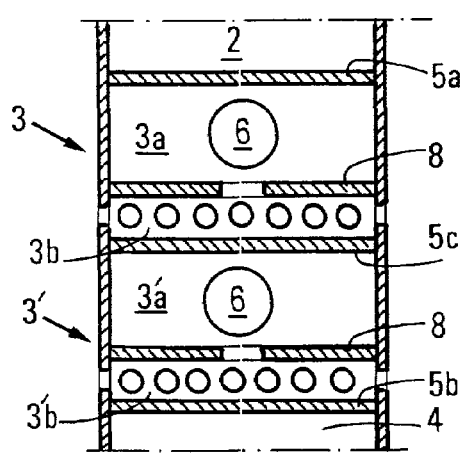
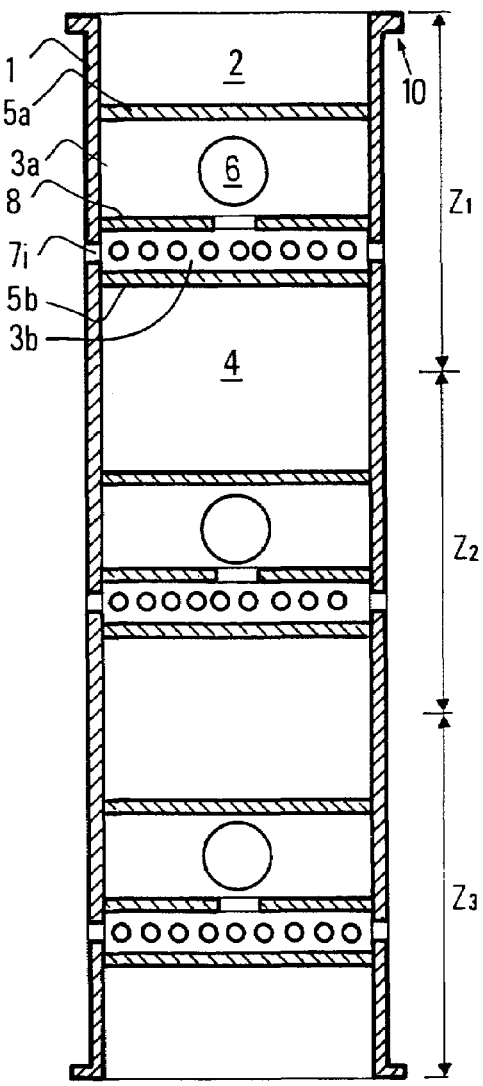
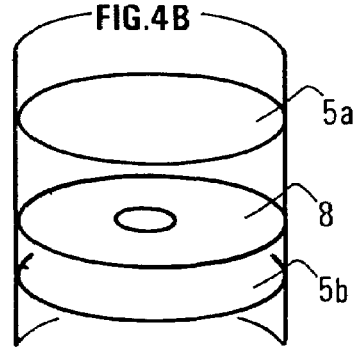

MAT ELEMENT THAT HAS A DISTRIBUTION FUNCTION

CROSS REFERENCE TO RELATED APPLICATION

This application is related to Applicants' concurrently filed application entitled "IMPROVED ROTARY VALVE", based on French Application 99/07.308 filed Jun. 9, 1999, now patent 6,537,451 issued Mar. 25, 2003.

This invention relates to a mat element that has in particular a collecting and/or distributing function of one or more fluids and a mat that consists of several elements.

The application of the invention is, for example, as a central mat for a large-diameter column that comprises heavy-weight elements, whereby the central mat at least partly absorbs the stresses arising from this weight.

The technological background is illustrated by the following documents: U.S. Pat. No. 5,462,719, U.S. Pat. No. 3,592,612, WO-A-9503867, EP-A-0472335 and EP-A-0074815.

In large-diameter columns, the central mats are used in particular to absorb the stresses of beams that are used to support fluid distribution plates or else the weight of a solid that fills the column. The solid can be a catalyst or an adsorbent that is distributed into, for example, several beds that are separated by plates or else by support elements.

Such a mat consists in general of a single part. When this mat is installed in a column or a chamber, it proves difficult to ensure its alignment along the central axis of the column. To solve this problem, it is known to use cables that hold the upper part of the mat along this central axis during the installation.

For separation columns by adsorption in which fluid circulations exist (injection, extraction or draw-off), the mat can be equipped with a fluid distribution device that comes, for example, in the form of a perforated ring that is mounted on the latter. Several conduits start from this ring to distribute and/or to draw off fluids in or from a distributing-collecting chamber.

In other applications, the central mat is used as a means for circulating one or more fluids to the panels that form the different distributors. Embodiments are described in, for example, Patents U.S. Pat. No. 2,369,478 and U.S. Pat. No. 2,461,331.

The central mat that consists of a single part has certain drawbacks, for example:
the difficulty of holding it in a strictly central or axial position in the column during its mounting,
complicating the assembly of the fluid distributors in a ring as soon as it is desired to maintain a constant speed of the fluid inside this central ring and having as symmetrical a fluid distribution as possible.

The object of this invention relates to a mat element that has in particular a distributing function and/or a collecting function and a mat that consists of several elements. The connection between the elements is carried out in particular with means that make it possible to ensure an approximately axial alignment along an axis of a column in which it is mounted.

This invention relates to a mat element or a beam element that comprises at least:
an upper part,
a distributor-collector part that comprises one or more secondary orifices and that comprises at least one main orifice, whereby the passage sections of secondary orifices and/or main orifice(s) are different,
a lower part,
the distributor-collector part or parts are arranged between an upper part and a lower part,
a sealing element that is arranged between the distributor-collector part and the upper part and a sealing element that is arranged between the distributor-collector part and the lower part,
a separation element that is arranged at the distributor-collector part, thus delimiting two spaces for circulation of fluids.

According to an embodiment, the mat element comprises, for example, a space $3c$ that is separate from spaces $3a$, $3b$, whereby said space $3c$ is connected to means for passing a fluid linking with the outside of the mat, and at least one means for passing a fluid, one of whose ends is arranged at the distributor-collector part and another end communicates with another mat element.

The mat element comprises, for example, several distributor-collector parts that are each provided with main and secondary orifices, whereby the different distributor-collector parts are arranged between an upper part and a lower part, whereby a distributor-collector part is separated from the other distributor-collector part by a sealing element, and each one of the distributor-collector parts comprises at least a space $3a$ and a space $3b$.

The mat element comprises, for example, at least one means for passing a fluid, whereby this means communicates with at least one of spaces $3a$ or $3b'$.

According to an embodiment, the beam element comprises, for example, one or more units, whereby each unit comprises at least:
an upper part,
a distributor-collector part that comprises one or more secondary orifices and that comprises at least one main orifice, whereby the passage sections of the main orifice and the secondary orifices are different,
a lower part,
the distributor-collector part or parts are arranged between an upper part and a lower part,
a sealing element that is arranged between the distributor-collector part and the upper part and a sealing element that is arranged between the distributor-collector part and the lower part,
a separation element that is arranged at the distributor-collector part, thus delimiting two spaces for circulation of fluids.

The beam element is, for example, approximately cylindrical.

According to an embodiment, the beam element comprises connecting means that are arranged at least at its lower end and/or its upper end.

The invention also relates to a mat that comprises one or more mat elements that have one of the above-mentioned characteristics on at least a portion of its length.

The invention also relates to a device for bringing at least one fluid into (contact with a solid, comprising at least:
one chamber,
a mat that is arranged approximately along the axis of said chamber,
several levels of distributor plates (Pi) that are spaced from one another,
a solid bed (Ai) that is arranged between two plates (Pi),
several transfer lines (Ti) for the circulation of fluids between the chamber and the outside of the chamber,
said nat comprises on at least a portion of its length a mat element that comprises at least the following characteristics:

an upper part,
 a distributor-collector part that comprises one or more secondary orifices and that comprises at least one main orifice, whereby the passage sections of the main orifice and secondary orifices are different,
 a lower part,
 the distributor-collector part or parts are arranged between the upper part and the lower part,
 a sealing element that is arranged between the distributor-collector part and the upper part and a sealing element that is arranged between the distributor-collector part and the lower part,
 a separation element that is arranged at the distributor-collector part, thus delimiting two spaces $3a$, $3b$ for circulation of fluids.

According to an embodiment, the device comprises one or more mat elements that comprise, for example, a space $3a$ that is separate from spaces $3a$, $3b$, whereby said space $3c$ is connected to means for passing a fluid that communicate with the outside of the mat, and at least one means for passing a fluid, one of whose ends is arranged at the distributor-collector part and another end communicates with another mat element.

The mat or mat elements can comprise several distributor-collector parts that are each provided with a main orifice and one or more secondary orifices, whereby the various distributor-collector parts are arranged between an upper part and a lower part, whereby a distributor-collector part is separated from another distributor-collector part by a sealing element, and each of the distributor-collector parts comprises at least a space $3a$ and a space $3b$.

The mat element or elements of the device for bringing it into contact comprises, for example, at least one means for passing a fluid that communicates with at least one of spaces $3a$ or $3b'$.

The device can comprise several secondary fluid transfer lines that are connected to said secondary passage means.

According to an embodiment, transfer lines ($T_i$) are connected to one or more means ($V_0$, $V_1$, $V_2$, $V_3$, V) that allow the circulation of different fluids between the outside of said chamber and the inside according to a determined sequence.

One of the means can be a rotary valve that makes it possible to link several groups of conduits: group $G_1$, group $G_2$ and group $G_3$, whereby said valve comprises at least:
 a stator that is provided with circulation means (E, F, R, S) of the fluid or fluids of group $G_1$, means for passing at least two fluids $F_1$, $F_2$ that belong to group $G_3$,
 a rotor that is equipped with means for passing fluids of group $G_3$ and also means that allow the linking either of fluids of group $G_1$ with group $G_3$ or of group $G_3$ with group $G_3$,
 the number of means for passing for fluid $F_1$ is approximately identical to the number of means for passing for fluid $F_2$, and said valve comprises means for linking at least two fluids of group $G_3$, in that passage section $S_1$ of openings for fluid $F_1$ is different from passage section $S_2$ of openings intended for fluid $F_2$.

The means for passing for fluid $F_1$ and for fluid $F_2$ have, for example, passage surface areas, respectively $S_1$ and $S_2$, and the $S_1/S_2$ ratio is approximately equal to 4, and, preferably, between 2 and 10.

The means of linking fluids of group $G_3$ can consist of slots that are arranged in a layer of material or liner that is deposited on the lower face of the rotor.

According to an embodiment, a slot has, for example, a depth "pe," and the value of the depth is at least equal to thickness "e" of the liner.

Circulation means (E, R, S, F) are formed by, for example, several grooves that are arranged on the support face of the stator, and the slots are arranged in, for example, the liner.

The number of circulation means (E, R, S, F) is, for example, 4.

According to an embodiment, plates ($P_i$) comprise several sectors of radial form, and each of the sectors comprises at least one fluid distribution chamber ($C_i$), whereby said fluid distribution chambers are connected to said central mat by said secondary fluid transfer lines.

The plates can also be precut into several sectors of tangential form, in that each of the sectors comprises at least one fluid distribution chamber, whereby said chambers are connected to said central mat by said secondary fluid transfer lines.

The device for bringing it into contact is advantageously used for the separation of at least one aromatic isomer with eight carbon atoms into a mixture of xylenes and ethylbenzene.

Figure 6:
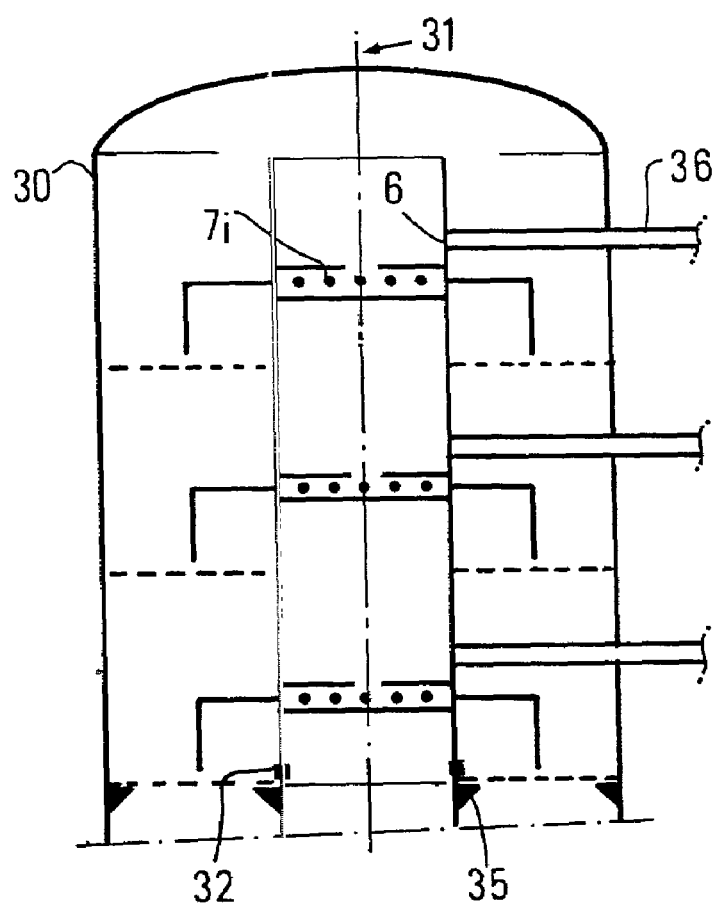
Figure 7:
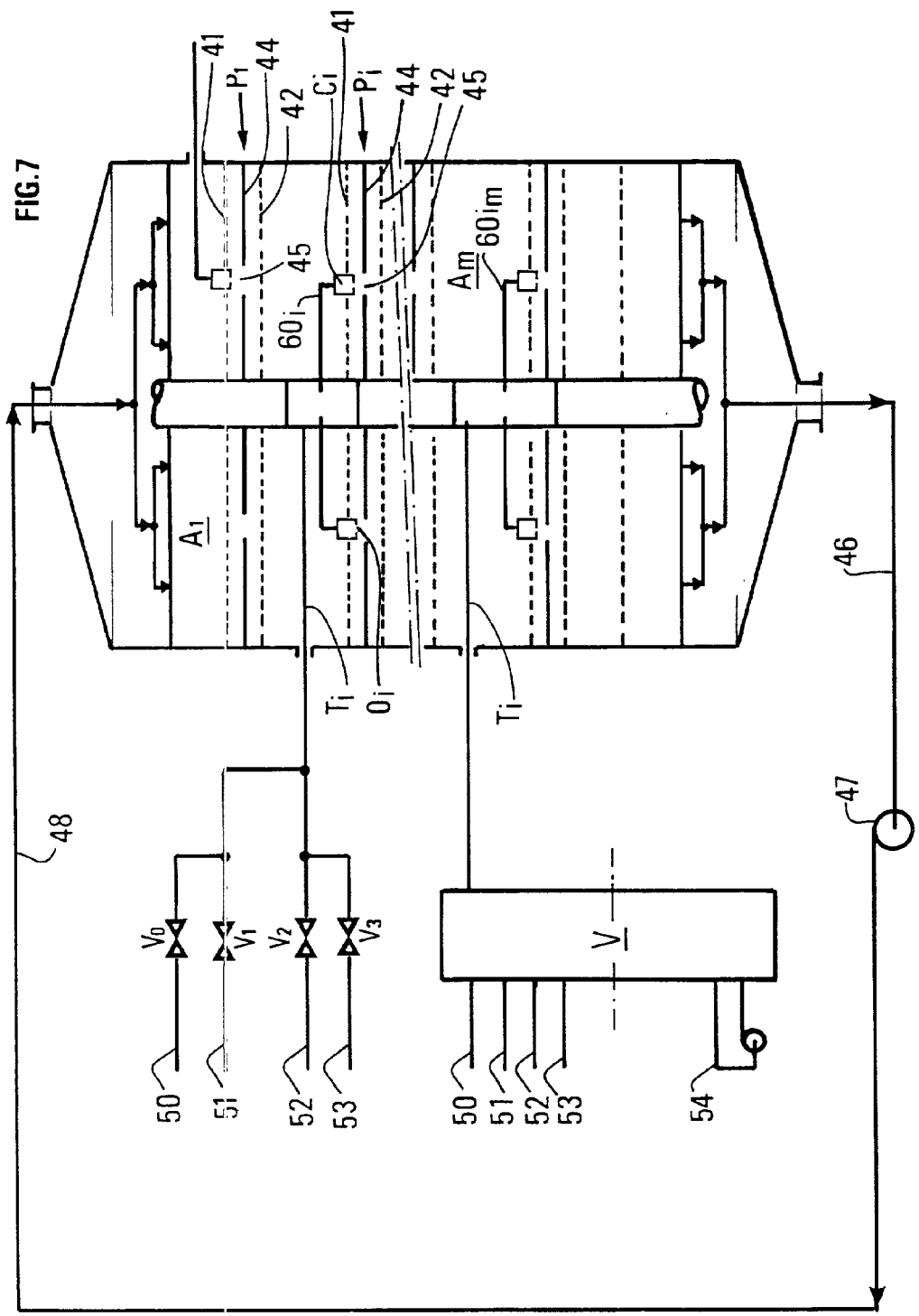
Figure 8:
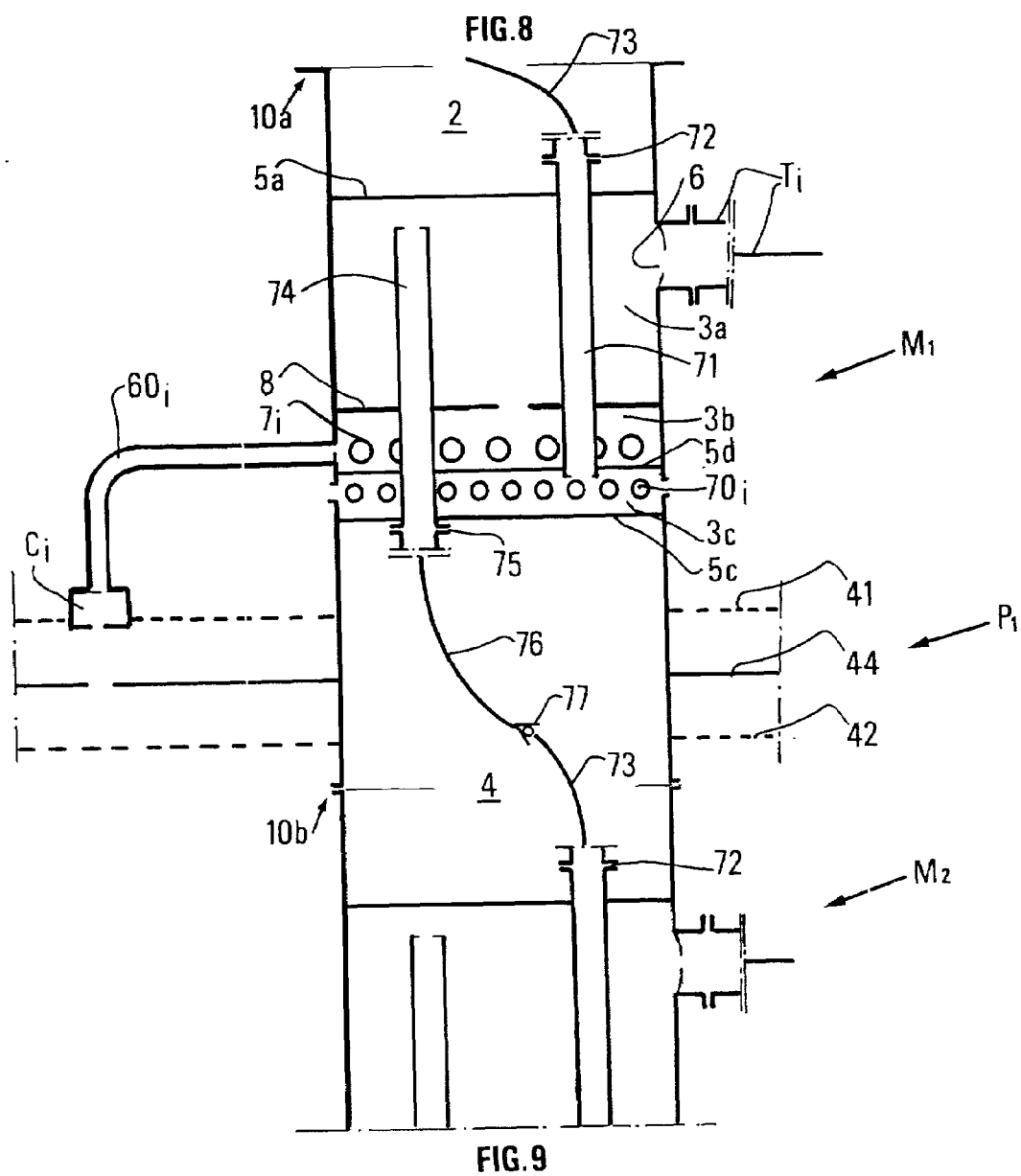
Figure 9:
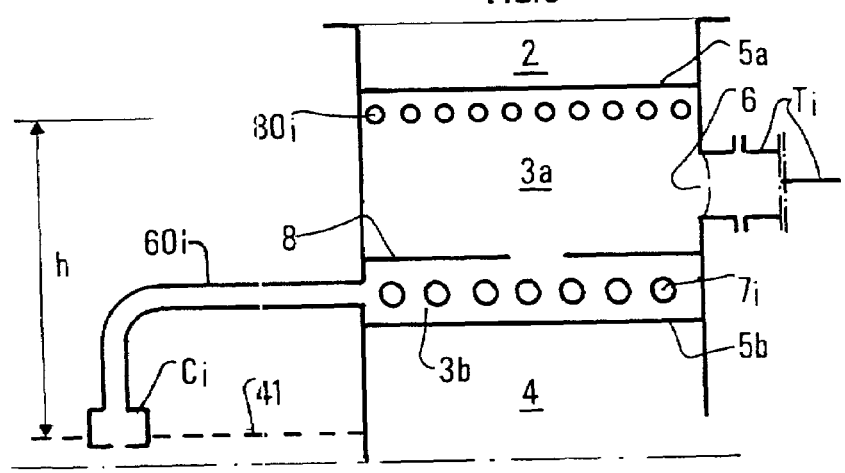
Figure 10:
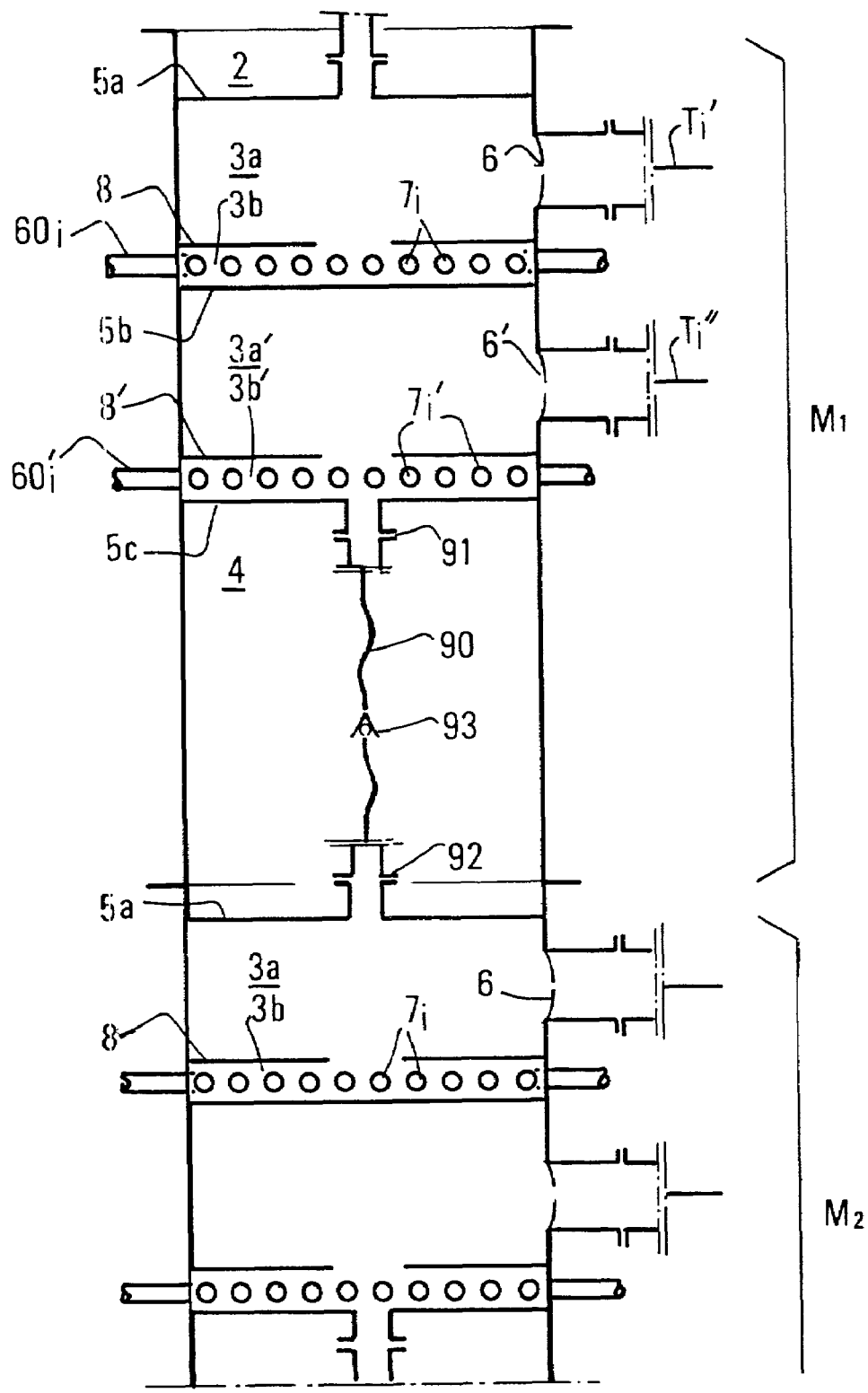
Figure 11:
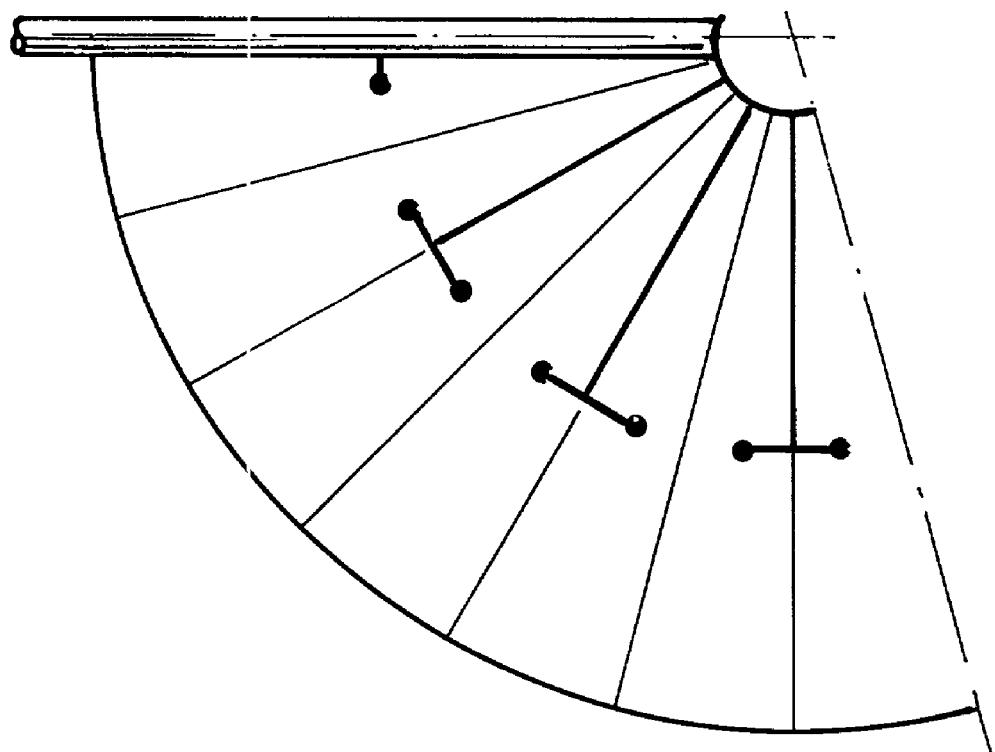
Figure 12:
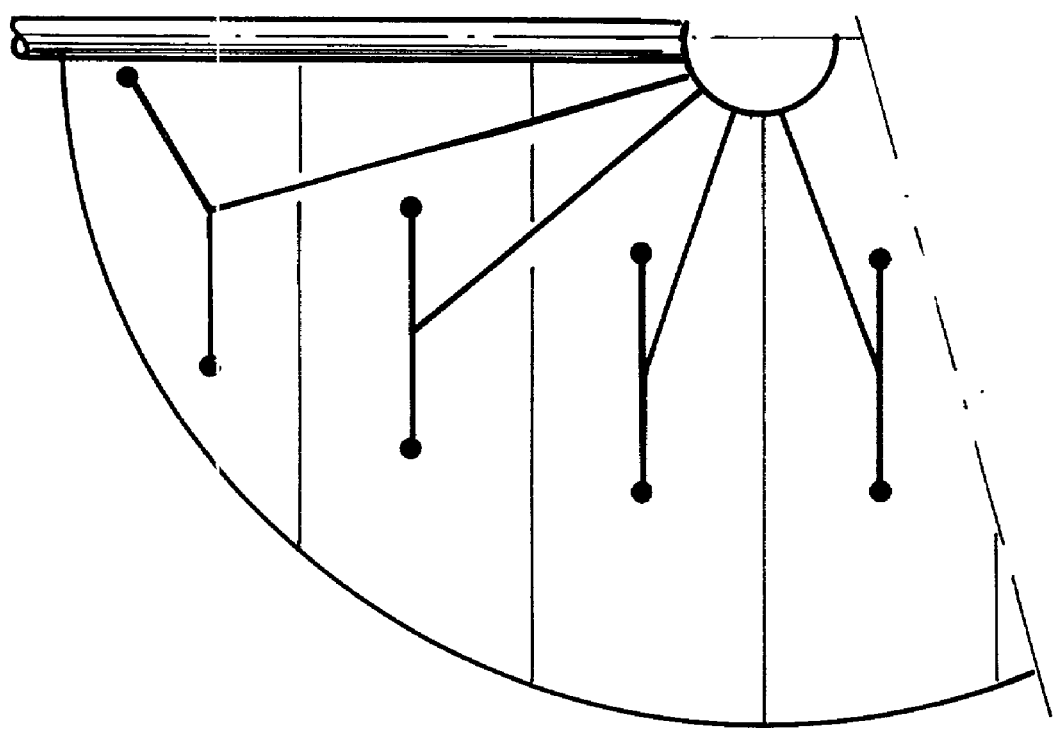

The invention will be better understood based on the following figures that illustrate, in a simplified and nonlimiting manner, several embodiments of the mat element and a central mat that is formed by several elements where:

FIGS. 1A and 1B show respectively a cutaway view and an example of a mat element along two planes, FIG. 2 shows a diagram of a first variant of the element of FIG. 1, FIG. 3 shows a variant of the element of FIG. 1 that comprises two means for passing and distributing fluids, FIG. 4A shows a diagram of a variant of a mat element of FIG. 1, and FIG. 4B shows a production possibility, FIG. 5 shows a chamber or column that comprises a central mat that is formed by several mat elements that are described in FIG. 1, FIG. 6 shows a diagram of a chamber that comprises a mat as described in FIG. 4A as well as its fluid circulation conduits, FIG. 7 shows a separation column that comprises a central mat, FIG. 8 shows a variant embodiment of the element that is described in FIG. 1A, FIG. 9 shows a variant of FIG. 8, FIG. 10 shows a variant embodiment of FIG. 3, FIGS. 11 and 12 show diagrams of variant embodiments of the device described in FIG. 7, and FIGS. 13, 14 and 15 show an example of a rotary valve that is used in the variant implementation described in FIG. 7 as well as a positioning example of the linking means.

FIGS. 1A and 1B show diagrams of a mat element according to the invention that consists of a tube 1 or an approximately cylindrical tube portion that has a wall thickness "e," a length "l," and an inside diameter $D_{int}$.

The mat element is formed by, for example, three parts: an upper part 2, an intermediate part 3 that for the comprehension of the description is designated fluid "distributor-collector" that comprises several means for passing one or more fluids, and a lower part 4. Parts 2 and 3 are separated by an upper sealing element $5a$, and parts 3 and 4 are separated by a lower sealing element $5b$, so that the fluids circulate only in part 3. In some cases, a minimal fluid fraction can optionally be present inside parts 2 or 4 to ensure a pressurization of the mat element, for example.

Distributor-collector element 3 is provided with different means that allow the passage or circulation of fluids from inside the cylindrical section to the outside and vice versa. These means are, for example, an orifice 6 that has a diameter $\phi_8$ and several orifices 7i with a diameter $\phi_7$, distributed over the periphery of element 1. A separation element 8, such as a plate that is provided with, for example, a central orifice 9, thus delimits two annular spaces 3a and 3b inside the distributor-collector element. Upper space 3a communicates with orifice 6, and lower space 3b communicates with orifices 7i.

When fluid distribution from the central beam element is considered, the fluid or fluids to be distributed flow from orifice 6 to the inside of the element then through orifice 9 before being distributed to the outside via orifices 7i.

Without exceeding the scope of the invention, it is also possible to reverse the functions of orifices 6 and 7i, whereby the fluid first passes through orifices 7i then orifice 8.

In its lower part and/or in its upper part, mat element 1 is provided with flanges respectively referenced 10a and 10b, or any other means that makes it possible to ensure the mechanical connection between the mat elements.

The elements can also be assembled by welding.

Separation element 8 can also consist of a perforated plate or else a grid.

The diameter of central orifice 9 is selected so as to obtain an adequate turbulence of the fluid or fluids inside spaces 3a and 3b to ensure a homogeneous distribution of the fluids through orifices 7i and 6.

Orifice 9 is preferably positioned in the center of plate 8 so that the fluid that is introduced via orifice 6 reaches the majority of orifices 7i at the same time.

When element 8 consists of a perforated plate that comprises several orifices, the sum of the passage surface area of the orifices is considered to ensure the most homogeneous distribution possible.

In some variant embodiments, parts 2 and 4 will be pressurized by using a fluid or a solid to obtain adequate stiffness relative to the feedstock to which the column is subjected.

Flanges 10a and 10b and the thickness of the mat will be designed to ensure the desired stiffness for the element of the column when it is acted on by the feedstock.

Mat element 1 as well as orifices 6 and 7i can have various shapes or geometries.

FIG. 2 shows a diagram of an embodiment of distributor-collector part 3 of one or more fluids.

Openings 7i are drilled into, for example, the mass of a part to generate several passage conduits 21i as well as a space 22 approximately at the center of the solid part. Space 22 communicates with conduits 21i, space 3a (FIG. 1A) and opening 6.

FIG. 3 shows a diagram of a variant embodiment of a mat element that comprises two distributor-collector parts 3 and 3' that comprise spaces that are referenced respectively 3a, 3b, and 3a', 3b' and that each have a structure that is similar to the one that is described in FIG. 1A. These two parts. These two parts 3 and 3' are stacked one above the other, and the whole structure is arranged between a lower part 4 and an upper part 2 so as to obtain a mat element. The sealing elements are referenced 5a, 5c, 5b by starting from upper part 3. The elements that bear references that are identical to elements that are described in FIGS. 1A and 3 have the same function.

FIG. 4A shows an example of a mat element that comprises, distributed over its length, three zones $Z_1$, $Z_2$ and $Z_3$ that each have a structure that is similar to the one that is provided in FIG. 1A.

The elements and the structure of each of zones $Z_1$, $Z_2$ and $Z_3$ are comparable to a mat element that is described in FIG. 1A.

The stages for producing such an element are, for example, as follows:

an approximately cylindrical hollow central tube is used, openings 6 and 7i are drilled spaced at predetermined intervals and with predetermined geometries, on the outside (FIG. 4B), the following different elements are combined: a lower sealing element 5b, then just above, a separation plate 8 and then another sealing element 5a, by spacing them so as to obtain a structure that is similar to the inside of the mat element that is described in FIG. 1. The first thing is to arrange the same elements starting from a given distance d between the lower sealing element of zone $Z_2$ and the upper sealing element of zone $Z_3$, for example, the whole structure that is thus formed is slipped into the hollow tube, and it is held with means that are known to one skilled in the art. The sealing between the plates and the hollow tube will be ensured by welding or any other means.

FIG. 5 shows a chamber that comprises a mat that consists of several elements of mat $M_i$ that have the characteristics that are described in FIG. 1A.

The different elements $M_i$ are stacked as inside chamber 30 along a vertical and central axis 31 of this chamber. To ensure the alignment along this axis, individual elements $M_i$ are provided with means 32 such that joints are arranged either at their lower end or at their upper end or else at the two ends. In particular, a particular feature of these joints is that they deform to make up an optionally axial offset of the mat when it is positioned inside a column, whereby the offset results from various elements that are mounted in the chamber and in particular plates that receive granular solids, such as an adsorbent. The joints thus also ensure the sealing.

The plates are put, for example, on support beams 35 that are integral with the central mat and with the inside wall of the chamber.

This FIG. 5 also shows a diagram of the linking means connecting with the central mat that also has a fluid-distributing or fluid-collecting function.

A main conduit 36 that is connected with orifice 5 empties into a mat element $M_i$. A fluid moves, for example, from a source that is outside of the chamber to the inside of the central tube via conduit 36 and orifice 6 to be distributed inside the chamber through openings 7i.

The distribution can be done directly starting from these openings, or else via conduits 37i that are each connected to an opening 7i and that empty into a distributing-collecting-mixing chamber.

The method for distribution is in particular based on the application or the process that is carried out in the chamber.

FIG. 6 shows a diagram of a column that is different from the one that is described in FIG. 5 only by the structure of its central mat.

The mat is formed by several mat elements that have a structure that is identical to the one that is described in FIG. 4A. The mat elements are assembled by joints that are similar to joints 32 that are described in FIG. 5. In this case, a conduit 36 is connected with an annular space (3a, 3a') (FIG. 3), whereby the number of these conduits per mat element is equal to the number of parts 3, 3' (FIG. 3) that constitute the mat element.

FIG. 7 shows a diagram in the same figure of two independent embodiments of a separation column equipped with a mat that consists of several elements as described in FIG. 1A.

The column makes it possible, for example, to carry out a separation by chromatography in a simulated moving bed. The two examples that are shown differ simply by the valves that are used to implement the sequences of the process and therefore the connections with the process fluids.

The mat element in this embodiment has a height that corresponds approximately to the height of an adsorbent bed $A_i$. The height of part $3a$ (FIG. 2) of the element is determined, for example, by taking into consideration the diameter of opening 6 that essentially corresponds to the diameter of transfer line Ti. The height of part $3b$ (FIG. 2) is defined relative to the diameters or sections of orifices $7i$. The values of the diameters of openings 6 and $7i$ are, for example, selected to minimize the dead volumes according to a method that is usually used by one skilled in the art that uses a linear speed criterion. The value of the criterion is, for example, between 4 and 12 m/s.

The column comprises an approximately cylindrical chamber 40 that is filled with an adsorbent that is distributed in several bed $A_1$ to $A_n$. A fluid distributor plate $P_i$ separates two consecutive adsorbent beds. A plate $P_i$ is formed from one or more panels, or DME, having as its function to distribute, extract and/or to mix one or more fluids.

A DME comprises in particular an upper grid 41 for holding the adsorbent bed, a chamber $C_i$ for distribution, extraction and/or mixing, a lower grid 42, means such as a baffle 44 that make it possible to separate lower grid 42 from upper grid 43, whereby baffle 44 is provided with a central opening $4b$, for example, that makes it possible for the fluids to circulate. In its lower part, chamber $C_i$ comprises, for example, one or more orifices $O_i$. These orifices $O_i$ allow the secondary fluid to pass, and the letter is either introduced into the following bed after having bean mixed with the main fluid that has run through the main bed, or drawn off via the suitable transfer line. A chamber $C_i$ is connected with the outside of the column via a distribution basket.

Various configurations can be considered for the panels or DME. The geometries that are described in Patent U.S. Pat. No. 5,792,346 of the applicant, for which the distributor panel comprises a single chamber for distributing, extracting and/or mixing one or more fluids, can be held for the panels.

The main fluid circulates along the longitudinal axis or main axis of the column, it is extracted via a conduit 46, recycled via a pump 47 and a conduit 48 to the top of the column. The column can be arranged along an approximately vertical axis or else an approximately horizontal axis. The main fluid flows to the inside of the column according to a piston or plug flow-type flow, whereby the composition and the flow front are essentially uniform at all points of the section of the column. A fluid distribution device (not shown in the figure) that is connected with conduit 48 optionally can equip the head of the column.

The chamber comprises a central beam or mat that consists of several elements as described in FIGS. 1A to 6, for example.

A chamber $C_i$ for distributing, extracting and/or mixing is connected with the outside of the column via a circuit that comprises at least one secondary transfer line that communicates with one of orifices $7i$ (FIG. 1A) of a mat element, whereby a main transfer line (Ti) links one of orifices 6 with a mat element.

Main transfer line Ti is connected to at least one line 50 for injecting feedstock, a line 51 for injecting desorbent, a line 52 for drawing-off an extract and a line 53 for drawing-off a raffinate by using, for example:

Upper part of the figure: means such as valves $V_0$, $V_1$, $V_2$, $V_3$ or else Lower part of the figure: a rotary valve V.

These different means make it possible to regulate the circulation of the process fluids according to a given sequence to carry out separation by chromatography.

First variant embodiment=use of four valves $V_0$, $V_1$, $V_2$, $V_3$ lower part of FIG. 7.

A transfer line Ti is connected with several process fluid transfer lines referenced 50, 51, 52 and 53 and equipped respectively with valves with indices $V_0$, $V_1$, $V_2$ and $V_3$ and controlled according to a given sequence to carry out the separation.

The fluid or fluids are distributed to distribution chambers $C_i$ by circulating through transfer line $T_i$ that is connected to orifice 6 of mat element 1, (orifices $7i$) and then via various lines $60i$ that communicate with these orifices $7i$ (FIG. 2).

The removal of the fluids is carried out, for example, starting from distribution chambers $C_i$ via the reverse path.

Second variant embodiment=use of a rotary valve—lower part of FIG. 7.

Rotary valve V is mounted between different lines 50, 51, 52 and 53 where the process fluids circulate and transfer line $T_i$ that empties into mat 1 through orifice 6.

The valve can also be connected to an input-output recycling line 54 that has a rinsing function that is known to one skilled in the art and that will not be described in detail.

The valves (individual valves $V_0$, $V_1$, $V_2$, $V_3$ or rotary valve V) are controlled sequentially by sequential switching means that are suitable for periodically advancing each injection point of the secondary fluid or for draw-off of the secondary fluid from a bed in the direction of the circulation of the main fluid, i.e., from top to bottom to ensure an operation in a simulated moving bed.

Without exceeding the scope of the invention, it is possible to equip a column of a mat that is formed by a set of elements as described in the preceding figures and also bypass lines that operate on a principle as given in Patent Application FR 97/16,273.

In the case of a column as described in FIG. 7 that is equipped with a distribution network and a circuit that makes it possible to carry out a bypass of a fraction of the main fluid, the mat can have a structure such as the one that is described in FIGS. 8, 9 and 10.

FIG. 8 shows a diagram of a mat element as described in FIG. 1A that is adapted to carry out the bypass of a fluid fraction.

Relative to FIG. 1A, a mat element also comprises a chamber or space referenced $3c$ that is arranged, for example, below space $3b$ and is isolated, on the one hand, from space $3b$ by a sealing element $5d$, and, on the other hand, lower element 4 via a sealing element $5c$.

FIG. 8 showed diagrams of two elements $M_1$ and $M_2$ to describe the arrangement of the bypass system and a plate $P_1$ that is arranged between the two.

At space $3c$, the wall of the mat is provided with means of passage such as orifices $70i$, distributed on the circumference of the periphery of the element.

The bypass fluid distribution circuit comprises:
a conduit 71 that empties into space $3c$ and runs through spaces $3b$, $3a$ and sealing element $5a$. Conduit 71 is connected by a flange 72 to a line 73 that is preferably flexible and located inside the mat in space 2 that is located above space 3, a conduit 74, one of whose ends is preferably arranged at space 3a, but that, without exceeding the scope of the invention, can be arranged at space 3b. Conduit 74 runs through space 3a (at least in part), and spaces 3b and 3c, separation means 8 and seals 5d and 5c. It is connected by a flange 75 to a line 76 that is preferably flexible and that extends inside the mat element. Line 76 connects, for example, conduit 74 of element $M_1$ to line 72 of element $M_2$. This line 76 can be equipped with a means that makes it possible to control the passing of fluid, for example a nonreturn valve 77.

The use of the flanges facilitates mounting flexible line 76 inside the mat before adjusting upper mat element $M_i$ via flange 75.

The bypass fluid is sampled starting from a plate $P_1$, passes through line 73 and hose 71, is introduced at space 3c and injected into the corresponding bed in plate $P_{i+1}$ via orifices 70i.

The flushing with the bypass fluid is limited to the volume of spaces 3a, 3d and 3c and inside lines $60_i$ of the column, whereby transfer line $T_i$ does not allow the passage of the bypass fluid.

Orifices 70i make it possible to generate an additional flow in the zone that is located on the periphery of the mat and just below secondary lines that are connected to orifices 7i in the encumbered zone where the main fluid flows poorly.

FIG. 9 describes a variant embodiment of FIG. 8 that comprises several orifices 80i that have a function that is identical to that of orifices 70i (FIG. 8) in the upper part of distributor-collector element 3. In this case, the bypass fluid is sampled on the same bed by orifices 80i, then circulates through spaces 3a and 3d, orifices 70i then secondary lines 60i for connection of the central mat to distribution chambers Ci of a distributor plate. The pressure drop in this implementation example corresponds in this case to the distance that separates orifices 70i and orifices 80i.

Another variant consists in arranging orifices 80i at secondary lines.

FIG. 10 shows a diagram of a variant embodiment that is adapted for a separation column that comprises two fluid distribution baskets and a bypass circuit.

To describe the arrangement of the bypass system, two stacked mat elements that are designated respectively $M_1$ and $M_2$ and that each comprise elements that are identical to those that are described in FIG. 3 are shown in this figure.

Elements $M_1$ and $M_2$ respectively comprise two spaces 3a and 3a' that each communicate with openings 6 and 6', transfer conduits Ti and Ti' as well as spaces 3b and 3b' that communicate with orifices that are referenced 7i and 7i'.

For its part, bypass circuit comprises a line 90 that has one of its ends connected to space 3b' of element $M_1$ via a flange 91, and its other end at space 3a of element $M_2$ via a flange 92. The flanges are for example, arranged at sealing elements 5c of element $M_1$ and 5a of element $M_2$. A nonreturn valve 93 that is mounted on line 90 allows the passage of fluid only from element $M_1$ to element $M_2$.

This system makes it possible to carry out a flushing by a bypass fluid at secondary lines, distribution chambers and inside the mat or support beam of the column.

A preferred embodiment of the invention consists in grouping the fluids two by two and circulating the extract and the desorbent in the same line, for example $T_i$, and the raffinate and the feedstock in another line, for example T'i. Actually, the bypass fluid does not circulate in the transfer lines.

FIGS. 11 and 12 show diagrams of two cutaway examples for plates Pi as well as their connection with the distributor or collector mat.

In FIG. 11, the plates have a radial cutaway whereas in FIG. 12, the cutaway is of the tangential type.

Figure 13:
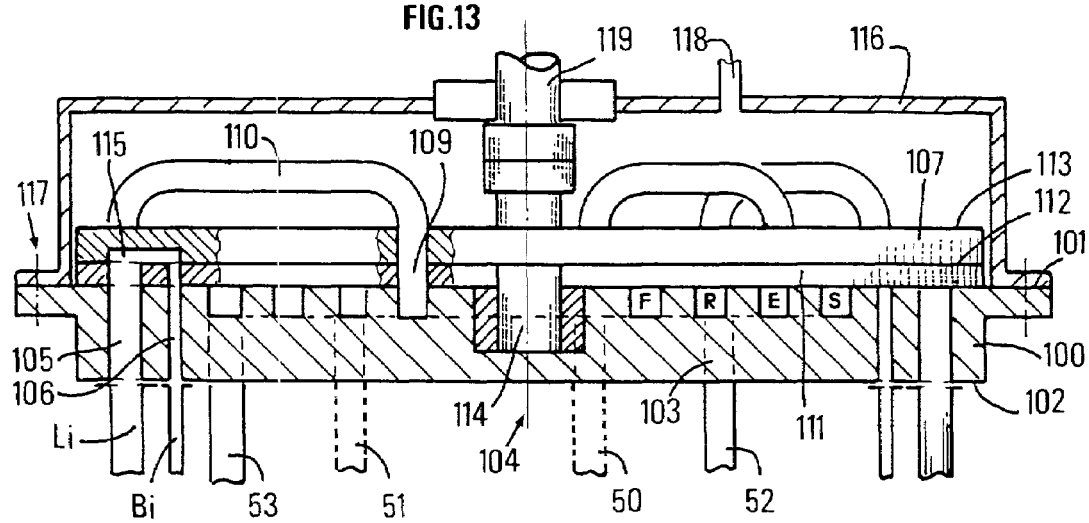
Figure 14:
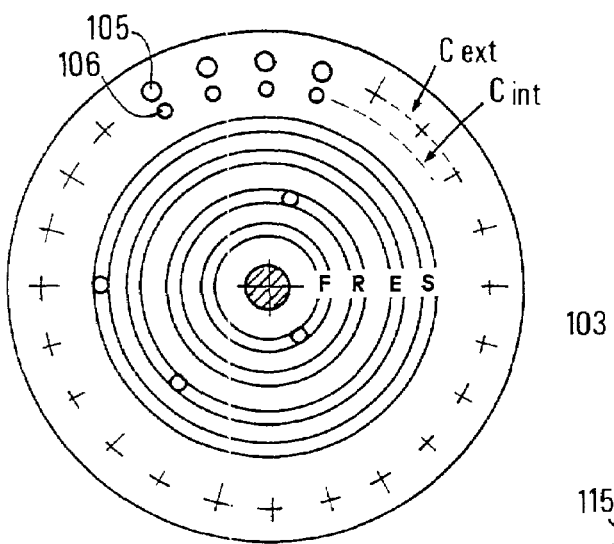
Figure 15:
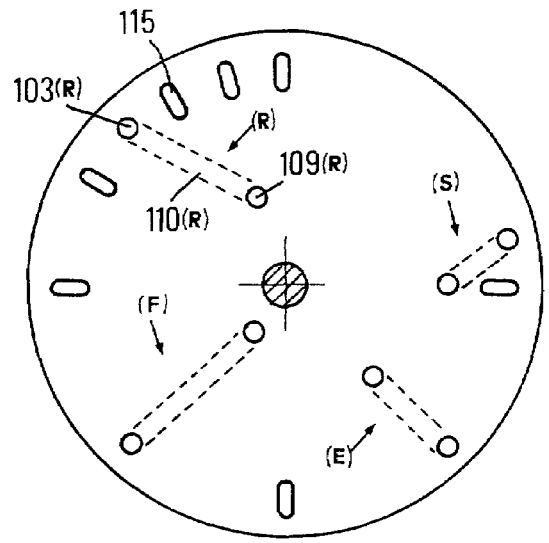

FIGS. 13, 14 and 15 make it possible to illustrate the valve according to the invention as well as an arrangement example of the means for communication for a given stage of the process.

The fluids that are involved in the process circulate through conduits that can be classified in three groups, defined, for example, according to their function. The connection between the different groups is carried out, for example, according to a predetermined sequence.

In a process for separation that uses four process fluids such as feedstock, extract, raffinate and desorbent, the different groups can be specified in the following manner:
  GROUP 1, $G_1$=the conduits that allow the transfer of fluids from said process fluids, such as extract, raffinate, feedstock and desorbent;
  GROUP 2, $G_2$=the conduits that allow the linking to be carried out between the different openings of the rotary valve;
  GROUP 3, $G_3$=the conduits that allow a process fluid to communicate with a bed of a separation column or between two beds (bypass fluid).

The concept of group that is defined for conduits can be extended to the fluids in question.

FIGS. 13 and 14 correspond to a cutaway view of the valve and a top view of the stator.

The rotary valve comprises:
  A stator 100 that comprises:
  +A part of thickness "$e_e$" delimited by an upper face 201 (support face) and a lower face 102.

Starting from the center of the stator, four approximately concentric grooves F, R, E, S are arranged on upper face 101. Each of these grooves is intended for the passage of a process fluid, whereby the distribution can be done according to an order of F, R, E, S or any other order. Each of the grooves is connected with a conduit 103 that runs through the thickness of the stator and allows the passage of, for example, process fluids that are obtained from conduits 50, 51, 52, 53.

In the description, grooves F, R, E, and S are part of predefined group $G_1$.

Different possibilities exist for circulating the fluids in the grooves. In FIGS. 13 and 14, the example shows a distribution of the fluids that ranges from more polluting to less polluting from center 104 to the periphery of the stator of the valve.

Several openings:
  Openings 105 that are each connected to a transfer line Li and with a passage surface $S_1$ are distributed, for example, on a circle $C_{ext}$ (FIG. 14) that is arranged toward the periphery of the stator. The number of these openings 105 is equal to the number of transfer conduits Li,
  openings 106 that are each connected with a bypass line (Bi) and with a passage section $S_2$, are arranged on a circle $C_{int}$ (FIG. 14) that is located between the circle that is outermost with respect to the stator and the first groove of the group (in this example groove F). An opening 106 corresponds to an opening 105.

Passage sections $S_1$ and $S_2$ of openings 105 and 106 are determined based on the flow rate of secondary fluids (or process fluids) and the flow rate of the bypass fluid; whereby the pressure drop is imposed by the granular medium for a given flow rate, and the diameter of the bypass line is selected to comply with synchronism of the flow rates of the main fluid and the bypass fluid. Typically, the value of the $S_1/S_2$ ratio is on the order of 4 and can be between 2 and 10.

A rotor 107 that comprises:

An element with thickness "$e_r$," delimited by a lower face 112 and an upper face 113. The element is mounted on a rotary shaft that comprises two parts 114 and 119 that are coupled to one another, Part 114 is held in the stator by bearings. Part 119 runs through a bell 116 that is described in detail below, whereby the sealing is ensured by systems that are known to one skilled in the art.

Several openings 109 that run through the rotor over its thickness. These openings 109 are arranged to link a groove (R, F, S, E) with a process fluid transfer line (50, 51, 52, 53), means 110 such that the "U"-shaped conduits for linking an opening 109 with an opening 105 of the stator. In this case of application, conduits 110 are four in number, a seal or liner 111, with thickness e, arranged on lower face 112 of the rotor, ensures the sealing between the four grooves, and various openings 105, 106, 103, means 115 for linking a transfer line Li with a bypass line Bi distributed on upper face 113. These means can consist of elliptical slots, for example, whose large axes are oriented, for example, radially to the rotor.

Slots 115 that are arranged in, for example, the liner have the following characteristics:

a depth "$p_e$,"

a main axis that has a sufficient length to link two openings 105 and 106 that are located on the same radius of the stator to produce the bypass. The length of this axis is at least equal to distance "d" that separates two circles $C_{int}$ and $C_{ext}$.

The value of depth "$p_e$" is, for example, greater than the value of thickness "e" of liner 111, whereby at least a portion of slot 115 is made in the liner that is arranged on lower face 112 of the rotor.

A bell 116:

Bell 116 is kept in the stator with means 117 that are known to one skilled in the art, such that screws, bolts or any other means make it possible to ensure a mechanical connection. A line 118 makes it possible to introduce a pressurized fluid. Prior to the rotation of the rotor, the pressure in the bell is lowered to reduce the force that is being exerted between the rotor and the stator and to facilitate the relative displacement between these two parts.

FIG. 14 shows the upper face of the stator, in particular the following elements: openings 105 and 106 that are distributed along two circles, respectively $C_{ext}$ and $C_{int}$, grooves F, R, E and S, and openings 103 that empty into the grooves.

FIG. 15 makes it possible to illustrate an example of linking various elements of the valve during a stage of the process. On the lower face of the rotor, the position of the slots and means 110 were shown when four beds experience the passing of four process fluids, whereas the other twenty beds channel the bypass fluid.

Slots 115 make it possible to let the bypass fluid pass between two consecutive beds, for example.

The four "U"-shaped conduits 110 link an opening of a groove with an outside conduit that allows the introduction or the removal of a process fluid.

Thus, in FIG. 15, the raffinate is removed from bed 4 by passing through an opening 109 (R), a conduit 110 (R), an opening 103 (R) and conduit 53, the feedstock is injected into bed 10 via conduit 50, an opening 103 (F), a conduit 110 (F), an opening 109 (F), the extract is drawn off from bed 16 by passing through an opening 109 (E), a conduit 110 (E), an opening 103 (E) and conduit 52, the solvent or desorbent is introduced into bed 20 via conduit 51, an opening 103 (S), a conduit 110 (S), an opening 109 (S).

Indices R, F, S and E respectively designate the raffinate, the feedstock, the desorbent and the extract.

The other beds receive the bypass fluid, which corresponds to linking an opening 105 with an opening 106 via a slot 115.

Without exceeding the scope of the invention, it is also possible to produce an elliptical slot in the liner at locations where the secondary fluids are injected or drawn off without exceeding the scope of the invention. In this case, the fluids are injected and drawn-off in part via the bypass line, but the four beds that follow the injections or the draw-offs do not undergo internal flow disturbance due to the interruption of the bypass flow.

What is claimed is:

1. A mat element (1) or beam element comprising at least:
   an elongated tube (1) and inside said tube
      an upper section (2) delimited by an upper zone of said tube,
      a distributor-collector part (3) comprising one or more secondary orifices (7i) and comprising at least one main orifice (6), whereby the passage sections of orifices (6) and (7i) are different, said distributor collector part (3) being delimited by an intermediate section of said tube beneath said upper section,
      a lower enclosure part (4) beneath said distributor-collector part (3) delimited by a lower section of said tube,
      a first sealing element (5a) arranged between said distributor-collector part (3) and said upper section (2) and a second sealing element (5b) arranged between said distributor-collector part (3) and said lower section (4), distributor and
      a separation element (8) arranged inside said distributor-collector part (3), thus delimiting two spaces (3a, 3b) for circulation of fluids.

2. A mat element according to claim 1, comprising means disposed in said tube delimiting a space (3c) that is separate from spaces (3a, 3b), whereby said space (3c) is connected to means (70i) for passing a fluid that communicates with the outside of the mat, and at least one means (74) for passing a fluid, one of whose ends is arranged at distributor-collector part (3) and another end communicates with another mat element.

3. A mat element according to claim 1, comprising several distributor-collector parts (3, 3') that are each provided with main orifices and secondary orifices (6, 7i), whereby different distributor-collector parts (3, 3') are arranged between an upper part (2) and a lower part (4), whereby part (3) is separated from part (3') by a sealing element, and each of parts (3) comprises at least said separation element 8 delimiting a space (3a) and a space (3b).

4. A mat element according to claim 3, comprising at least one means (90) for passing a fluid that communicates with at least one of spaces (3a) or (3b').

5. A beam element according to claim 1, comprising a plurality of units, each comprising at least:
- an upper section (2),
- a distributor-collector part (3) comprising one or more secondary orifices (7$i$) and comprising at least one main orifice (6), whereby the passage sections of orifices (6) and (7$i$) are different,
- a lower enclosure part (4),
- distributor-collector part or parts (3) arranged between said upper part (2) and said lower enclosure part (4),
- a sealing element (5$a$) arranged between distributor-collector part (3) and said upper part (2) and a sealing element (5$b$) arranged between distributor-collector part (3) and said lower part (4),
- a separation element (8) arranged inside distributor-collector part (3), thus delimiting two spaces (3$a$, 3$b$) for circulation of fluids.

6. A mat element according to claim 1, comprising an approximately cylindrical beam element.

7. A mat element according to claim 1, comprising connecting means (10$a$, 10$b$) arranged at at least its lower end and/or its upper end for connecting to another mat element.

8. A device for bringing at least one fluid into contact with a solid, comprising at least:
- one chamber (40),
- a mat arranged approximately along the axis of said chamber,
- several spaced levels of distributor plates (P$i$),
- a solid bed (A$i$) arranged between two plates (P$i$),
- several transfer lines (T$i$) for the circulation of fluids between the chamber and the outside of the chamber,
- said mat comprising on at least a portion of its length a mat element comprising at least the following characteristics:
  - an upper section (2) delimited by an upper zone of said tube,
  - a distributor-collector part (3) that comprises one or more secondary orifices (7$i$) and that comprises at least one main orifice (8), whereby the passage sections of orifices (6) and (7$i$) are different, said distributor collector part (3) being delimited by an intermediate section of said tube beneath said upper section,
  - a lower enclosure part (4) beneath said distributor-collector part (3) delimited by a lower section of said tube,
  - a first sealing element (5$a$) arranged between said distributor-collector part (3) and said upper section (2) and a second sealing element (5$b$) arranged between said distributor-collector part (3) and said lower section (4), whereby said sealing elements permit fluid circulation substantially only in said distributor-collector part (3), and
  - a separation element (8) arranged inside said distributor-collector part (3), thus delimiting two spaces (3$a$, 3$b$) for circulation of fluids.

9. A device according to claim 8, wherein said mat element or elements comprise means disposed in said tube delimiting a space (3$c$) that is separate from spaces (3$a$, 3$b$), whereby said space (3$c$) is connected to means (70$i$) for passing a fluid that communicates with the outside of the mat, and at least one means (74) for passing a fluid, one of whose ends is arranged at distributor-collector part (3) and another end communicates with another mat element.

10. A device according to claim 8, wherein said mat element or elements comprise several distributor-collector parts (3, 3') that are each provided with orifices (6, 7$i$), whereby different distributor-collector parts (3, 3') are arranged between an upper part (2) and a lower part (4), whereby part (3) is separated from part (3') by a sealing element, each of parts (3) comprises said separation element delimiting at least a space (3$a$) and a space (3$b$).

11. A device according to claim 10, wherein said mat element or elements comprises at least one means (90) for passing a fluid that communicates with at least one of spaces (3$a$) or (3$b$').

12. A device according to claim 8, comprising several secondary fluid transfer lines (60$i$) connected to secondary passage means.

13. A device according to claim 8, comprising transfer lines (T$i$) connected to one or more means (V$_0$, V$_1$, V$_2$, V$_3$, V) that allow the circulation of various fluids between the outside of said chamber and the inside according to a given sequence.

14. A device according to claim 13, comprising a rotary valve for linking several groups of hoses: group G$_1$, group G$_2$ and group G$_3$, whereby said valve comprises at least:
- a stator (100) provided with circulation means (E, F, R, S) of the fluid or fluids of group G$_1$, means (105, 106) for passing at least two fluids F$_1$, F$_2$ that belong to group G$_3$,
- a rotor (107) equipped with means (109) for passing fluids of group G$_3$ and also means (110) that allow the linking either of fluids of group G$_1$ with group G$_3$ or of group G$_3$ with group G$_3$,
- the number of means (105) for passing for fluid F$_1$ is approximately identical to the number of means (106) for passing for fluid F$_2$, and said valve comprises means (102) for linking at least two fluids of group G$_3$, wherein passage section S$_1$ of openings for fluid F$_1$ is different from passage section S$_2$ of openings intended for fluid F$_2$.

15. A device according to claim 14, wherein the passage means of the rotary valve for fluid F$_1$ and for fluid F$_2$ have passage surface areas, respectively S$_1$ and S$_2$, and wherein the S$_1$/S$_2$ ratio is approximately equal to 4 and preferably between 2 and 10.

16. A device according to claim 14, wherein said means for linking the rotary valve of the fluids of group G$_3$ comprises slots (112) arranged in a layer of material or a liner deposited on the lower face of the rotor.

17. A device according to claim 16, wherein slots (112) of said valve have a depth "pe" and wherein said depth is at least equal to thickness "e" of the liner.

18. A device according to claim 16, wherein said circulation means (E, R, S, F) of said rotary valve are formed from several grooves arranged on the support face of the stator and wherein the slots are arranged in the liner.

19. A device according to claim 14, wherein said circulation means (E, R, S, F) of said rotary valve are four in number.

20. A device according to claim 12, wherein said plates (P$i$) comprise several sectors of radial form and wherein each of the sectors comprises at least one fluid distribution chamber (C$i$), whereby said fluid distribution chambers are connected to said central mat by said secondary fluid transfer lines (60$i$).

21. A device according to claim 12, wherein said plates are precut into several sectors of tangential form, and each of the sectors comprises at least one fluid distribution chamber, whereby said chambers are connected to said central mat by said secondary fluid transfer lines.

22. A method for the separation of at least one aromatic isomer with eight carbon atoms into a mixture of xylenes and ethylbenzene, said method comprising utilizing the device of claim 8.

23. A device for bringing at least one fluid into contact with a solid, comprising at least:
one chamber (40),
a mat arranged approximately along the axis of said chamber,
several spaced levels of distributor plates (Pi),
a solid bed (Ai) arranged between two plates (Pi),
several transfer lines (Ti) for the circulation of fluids between the chamber and the outside of the chamber,
said mat comprising on at least a portion of its length a mat element comprising at least the following characteristics:
an upper part (2),
a distributor-collector part (3) that comprises one or more secondary orifices (7*i*) and that comprises at least one main orifice (8), whereby the passage sections of orifices (6) and (7*i*) are different,
a lower part (4),
distributor-collector part or parts (3) are arranged between said upper part (2) and said lower part (4),
a sealing element (5*a*) arranged between distributor-collector part (3) and upper part (2) and a sealing element (5*b*) arranged between distributor-collector part (3) and lower part (4),
a separation element (8) arranged at distributor-collector part (3), thus delimiting two spaces (3*a*, 3*b*) for circulation of fluids, said device further comprising a rotary valve for linking several groups of hoses: group $G_1$, group $G_2$ and group $G_3$, whereby said valve comprises at least:
a stator (100) provided with circulation means (E, F, R, S) of the fluid or fluids of group $G_1$, means (105, 106) for passing at least two fluids $F_1$, $F_2$ that belong to group $G_3$,
a rotor (107) equipped with means (109) for passing fluids of group $G_3$ and also means (110) that allow the linking either of fluids of group $G_1$ with group $G_3$ or of group $G_3$ with group $G_3$,
the number of means (105) for passing for fluid $F_1$ is approximately identical to the number of means (106) for passing for fluid $F_2$, and said valve comprises means (102) for linking at least two fluids of group $G_3$, wherein passage section $S_1$ of openings for fluid $F_1$ is different from passage section $S_2$ of openings intended for fluid $F_2$.

24. A device according to claim 23, wherein the passage means of the rotary valve for fluid $F_1$ and for fluid $F_2$ have passage surface areas, respectively $S_1$ and $S_2$, and wherein the $S_1/S_2$ ratio is approximately equal to 4 and preferably between 2 and 10.

25. A device according to claim 23, wherein said means for linking the rotary valve of the fluids of group $G_3$ comprises slots (112) arranged in a layer of material or a liner deposited on the lower face of the rotor.

26. A device according to claim 25, wherein slots (112) of said valve have a depth "pe" and wherein said depth is at least equal to thickness "e" of the liner.

27. A device according to claim 23, wherein said circulation means (E, R, S, F) of said rotary valve are formed from several grooves arranged on the support face of the stator and wherein the slots are arranged in the liner.

28. A device according to claim 23, wherein said circulation means (E, R, S, F) of said rotary valve are four in number.

29. A device for bringing at least one fluid into contact with a solid, comprising at least:
one chamber (40),
a mat arranged approximately along the axis of said chamber,
several spaced levels of distributor plates (Pi),
a solid bed (Ai) arranged between two plates (Pi),
several transfer lines (Ti) for the circulation of fluids between the chamber and the outside of the chamber,
said mat comprising on at least a portion of its length a mat element comprising at least the following characteristics:
an upper part (2),
a distributor-collector part (3) that comprises one or more secondary orifices (7*i*) and that comprises at least one main orifice (8), whereby the passage sections of orifices (6) and (7*i*) are different,
a lower part (4),
distributor-collector part or parts (3) are arranged between said upper part (2) and said lower part (4),
a sealing element (5*a*) arranged between distributor-collector part (3) and upper part (2) and a sealing element (5*b*) arranged between distributor-collector part (3) and lower part (4),
a separation element (8) arranged at distributor-collector part (3), thus delimiting two spaces (3*a*, 3*b*) for circulation of fluids, and further comprising several secondary fluid transfer lines (60*i*) connected to secondary passage means and wherein said plates (Pi) comprise several sectors of radial form and wherein each of the sectors comprises at least one fluid distribution chamber (Ci), whereby said fluid distribution chambers are connected to said central mat by said secondary fluid transfer lines (60*i*).

30. A device according to claim 29, wherein said plates are precut into several sectors of tangential form, and each of the sectors comprises at least one fluid distribution chamber, whereby said chambers are connected to said central mat by said secondary fluid transfer lines.

31. A method for the separation of at least one aromatic isomer with eight carbon atoms into a mixture of xylenes and ethylbenzene, said method comprising separating said mixture in a system comprising:
one chamber (40),
a mat arranged approximately along the axis of said chamber,
several spaced levels of distributor plates (Pi),
a solid bed (Ai) arranged between two plates (Pi),
several transfer lines (Ti) for the circulation of fluids between the chamber and the outside of the chamber,
said mat comprising on at least a portion of its length a mat element comprising at least the following characteristics:
an upper part (2),
a distributor-collector part (3) that comprises one or more secondary orifices (7*i*) and that comprises at least one main orifice (8), whereby the passage sections of orifices (6) and (7*i*) are different,
a lower part (4),
distributor-collector part or parts (3) are arranged between said upper part (2) and said lower part (4),
a sealing element (5*a*) arranged between distributor-collector part (3) and upper part (2) and a sealing element (5*b*) arranged between distributor-collector part (3) and lower part (4), a separation element (8) arranged at distributor-collector part (3), thus delimiting two spaces (3*a*, 3*b*) for circulation of fluids.

32. A mat element according to claim 1, wherein said first and second sealing elements are imperforate solid disks transverse to the longitudinal axis of said elongated tube.

33. A mat element according to claim 1, said separation element being a plate having at least one orifice (9) permitting communication between said two spaces (3*a*, 3*b*) said separation element in combination with said sealing element, said one or more secondary orifices (7*i*) and said main orifice (6), permitting a fluid to pass successively from the main orifice (6) into space 3*a*, through orifice (9) into space 3*b* and through orifices (7*i*), or in the reverse direction.

\* \* \* \* \*